United States Patent
Xiang et al.

(10) Patent No.: US 6,897,233 B2
(45) Date of Patent: May 24, 2005

(54) PEPTIDE DEFORMYLASE INHIBITORS

(75) Inventors: Jia-Ning Xiang, Palo Alto, CA (US);
Siegfried B. Christensen, IV,
Collegeville, PA (US); Xiangmin Liao,
Collegeville, PA (US); Maxwell D. Cummings, Strafford, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 185 days.

(21) Appl. No.: 10/469,560

(22) PCT Filed: Mar. 1, 2002

(86) PCT No.: PCT/US02/06261
§ 371 (c)(1),
(2), (4) Date: Aug. 29, 2003

(87) PCT Pub. No.: WO02/070654
PCT Pub. Date: Sep. 12, 2002

(65) Prior Publication Data
US 2004/0077856 A1 Apr. 22, 2004

Related U.S. Application Data

(60) Provisional application No. 60/272,569, filed on Mar. 1, 2001.

(51) Int. Cl.$^7$ .................... C07D 207/12; A61K 31/40
(52) U.S. Cl. ........................ 514/424; 548/550
(58) Field of Search ................. 548/550; 514/424

(56) References Cited

U.S. PATENT DOCUMENTS 5,712,300 A * 1/1998 Jacobsen .................... 514/389

FOREIGN PATENT DOCUMENTS

WO          WO 00/59285        10/2000

* cited by examiner

Primary Examiner—Fiona T. Powers
(74) Attorney, Agent, or Firm—Soma G. Simon; Mary McCarthy; Charles M. Kinzig

(57) ABSTRACT

PDF inhibitors and novel methods for their use are provided.

3 Claims, 1 Drawing Sheet

PEPTIDE DEFORMYLASE INHIBITORS

This application is the National Stage of International Application No. PCT/US02/06261 filed 1 Mar. 2002, which claims the benefit of Provisional application No. 60/272,569 filed 1 Mar. 2001.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formylmethionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

To date, polypeptide deformylase homologous genes have been found in bacteria, in chloroplast-containing plants, in mice and in humans. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cyteine and two histidines which are required to coordinate the active site metal (Meinnel, T. et al, 1997, Journal of Molecular Biology, 267, 749–761).

PDF is recoginzed to be an attractive anti-bacterial target, as this enzyme has been demonstrated to be essential for bacterial growth in vitro (Mazel, D. et al, EMBO J. 13 (4), 914–923, 1994), is not believed to be involved in eukaryotic protein synthesis (Rajagopalan et al, J. Am. Chem. Soc. 119, 12418–12419, 1997), and is universally conserved in prokaryotes (Kozak, M. Microbiol. Rev. 47, 1–45, 1983). Therefore PDF inhibitors can potentially serve as broad spectrum anti-bacterial agents.

SUMMARY OF THE INVENTION

The present invention involves novel anti-bacterial compounds represented by Formula (I) hereinbelow and their use as PDF inhibitors.

The present invention further provides methods for inhibiting PDF in an animal, including humans, which comprises administering to a subject in need of treatment an effective amount of a compound of Formula (I) as indicated hereinbelow.

DETAILED DESCRIPTION OF THE INVENTION

Figure 1:
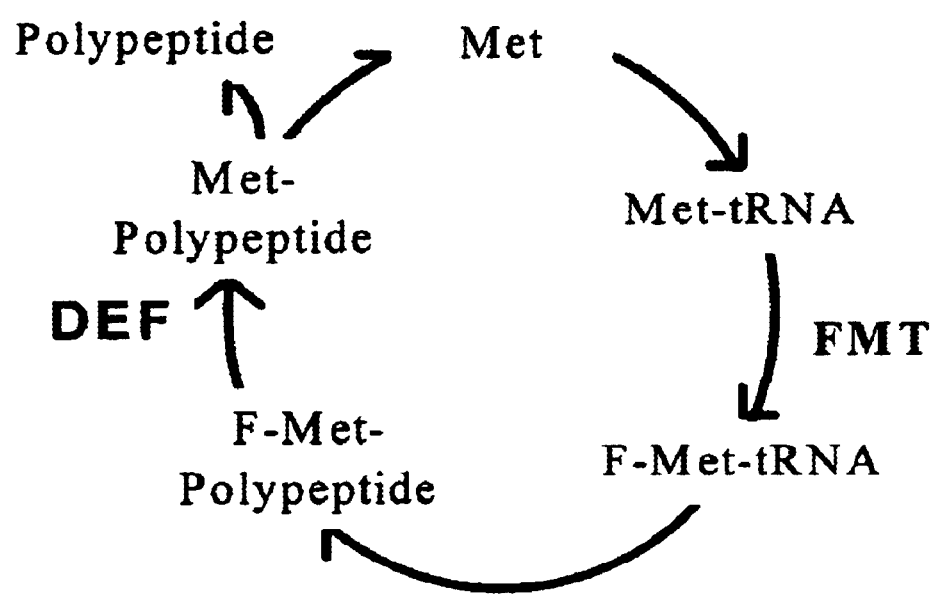
FIG. 1 illustrates the series of reactions referred to as the methionine cycle.

The compounds useful in the present methods are selected from Formula (I) hereinbelow:

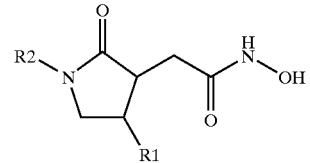

(I)

wherein:

R1 is selected from the group consisting of $C_{1-6}$alkyl, —$C_{1-2}$alkylAr, and Ar;

R2 is selected from the group consisting of hydrogen, $C_{1-6}$alkyl, —$(CH_2)_m$OH, —$(CH_2)_n$Ar', —$(CH_2)_n$Het, —Ar', —$SO_2$R3, —C(O)R3, —C(O)NHR3, —C(O)OR3, —CH(R4)CONR5R6, and —CH(R4)$CO_2$R7;

R3 is selected from the group consisting of $C_{1-6}$alkyl, —$C_{1-2}$alkylAr', and Ar';

R4 is hydrogen, or $C_{1-6}$alkyl;

R5 and R6 are independently selected from the group consisting of hydrogen, $C_{1-6}$alkyl, —$C_{1-2}$alkylAr', and Ar'; and R5, R6 together form a five or six membered cycloalkyl ring which is optionally mono-substituted by —$CH_2$OR7;

R7 is selected from the group consisting of hydrogen, and $C_{1-3}$alkyl;

Ar is selected from the group consisting of phenyl, furyl, and thienyl, all of which may be optionally substituted by one or more $Z_1$ groups;

Ar' is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl, all of which may be optionally substituted by one or more $Z_2$ groups; Het is selected from the group consisting of tetrahydrofuranyl and piperidinyl;

$Z_1$ is independently selected from the group consisting of $C_{1-3}$alkyl, —CN, F, Cl, Br, and I;

$Z_2$ is independently selected from the group consisting of $C_{1-6}$alkyl, —OR2, —$(CH_2)_n$$CO_2$R4, —C(O)NR5R6, —CN, —$(CH_2)_n$OH, —$NO_2$, F, Cl, Br, I, —NR5R6, and —NHC(O)R1;

m is 2 to 5;

and n is 0 to 5.

As used herein, "alkyl" refers to a hydrocarbon group joined together by single carbon-carbon bonds. The alkyl hydrocarbon group may be linear, branched or cyclic.

Preferred compounds useful in the present invention are selected from the group consisting of:

2-[4-Butyl-1-(5-hydroxypentyl)-2-oxopyrrolidin-3-yl]-N-hydroxyacetamide;

2-[(3R,4R)-4-Butyl-1-(5-hydroxypentyl)-2-oxopyrrolidin-3-yl]-N-hydroxyacetamide; and 2-[(3S,4S)-4-Butyl-1-(5-hydroxypentyl)-2-oxopyrrolidin-3-yl]-N-hydroxyacetamide.

Also included in the present invention are pharmaceutically acceptable salts and complexes, such as the hydrochloride, hydrobromide and trifluoroacetate salts, and the sodium, potassium and magnesium salts. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of formula (I):

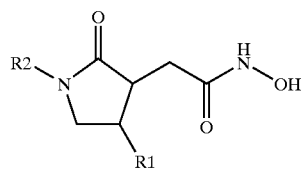
(I)

that can be prepared by a process consisting of:
treating an unsaturated lactone of Formula (2)

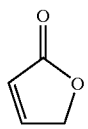
(2)

with, e.g., a Grignard reagent R1MgX in the presence of catalytic ammount of a copper salt, such as copper (I) bromide, HMPA and chlorotrimethylsilane at an appropriate temperature, to afford a lactone of Formula (3).

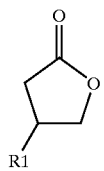
(3)

Treatment of a lactone of Formula (3) with bromine in the presence of a catalytic amount of phosphorous tribromide and dimethylformamide, followed by treatment with thionyl chloride, gives a compound of Formula (4).

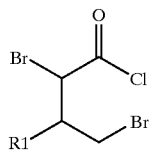
(4)

Reaction of an acid chloride of Formula (4) with an amine of Formula (5)

(5)

in a suitable solvent, such as chloroform, in the presence of a base, such as sodium hydroxide, followed by cyclization with, e.g., sodium hydride in refluxing toluene, affords a lactam of Formula (6).

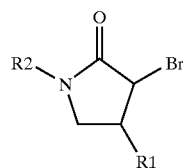
(6)

Reacting an α-bromo-lactam of Formula (6) with, e.g., the sodium salt of t-butyl methyl malonate in a suitable solvent, such as dimethylformamide, followed by decarboxylation in refluxing toluene in the presence of catalytic amount of p-toluenesulfonic acid, affords a compound of Formula (7).

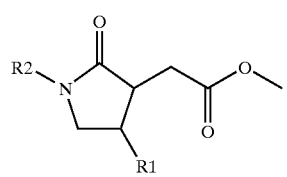
(7)

Removal of the protecting group (if any) in R1 and/or R2, followed by treatment with 50% hydroxylamine in water in a suitable solvent, such as dioxane, affords a racemic compound of Formula (I).

A bromo-lactam of Formula (6) can be converted to a des-bromo compound of Formula (8) using an appropriate reducing agent, such as sodium borohydride, in an appropriate solvent.

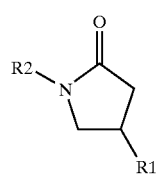
(8)

Alternatively, an intermediate of Formula (8) can be prepared starting from an aldehyde of Formula (9)

(9)

that is reacted with Ph$_3$P=CHCO$_2$Et in a solvent, such as tetrahydrofuran, to give an α,β-unsaturated ester of Formula (10).

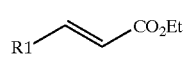
(10)

Treatment of a compound of Formula (10) with nitromethane in presence of Triton B leads to a Michael addition product of Formula (11).

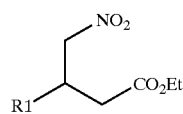
(11)

Reduction of the nitro group in a compound of Formula (11) under hydrogenation conditions and intramolecular cyclization, at appropriate temperature in an appropriate solvent, such as toluene, affords a lactam of Formula (8)

wherein R2=H, which can be converted to a compound of Formula (8) wherein R2 is other than H through an alkylation reaction.

The lactam nitrogen of a compound of Formula (8) wherein R2=H can be protected using an appropriate protecting group, such as a Boc group, under standard conditions to give a versatile intermediate of Formula (12).

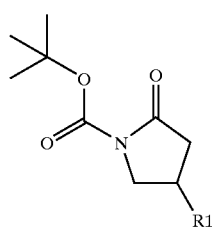
(12)

Treatment of an enolate generated from a lactam of Formula (8) with an appropriate alkylating agent, such as ethyl bromoacetate, in an appropriate solvent, such as dry tetrahydrofuran, affords an ester of Formula (13).

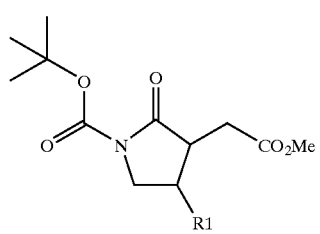
(13)

Removal of the Boc group from compounds of Formula (13) using an appropriate acid, such as trifluoroacetic acid, gives a compound of Formula (14).

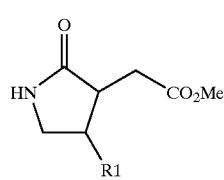
(14)

A lactam of Formula (14) is then readily converted to the target compound of Formula (I) by treatment with an alkyl halide, a sulfonyl chloride, an acid chloride or an isocyanate followed by treatment with a 50% hydroxyamine solution.

An optically active compound of Formula (I) can be prepared by treating a lactone of Formula (3) with a chiral amine, such as (S)-methylphenyl amine, in the presence of a catalyst, such as 2-hydroxypyridine, in a suitable solvent, such as toluene, at reflux to afford a mixture of two diastereomers of Formula (15) and (16), which can be readily separated by silica gel flash column chromatography.

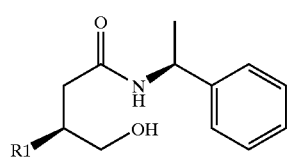
(15)

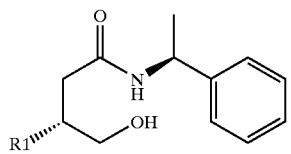
(16)

Intramolecular Mitsunobu reaction of a compound of Formula (15) or (16) affords a lactam of Formula (17) or (18), respectively.

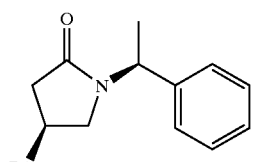
(17)

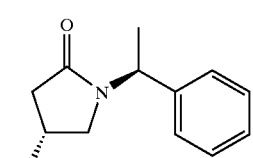
(18)

Removal of the N-protecting group of lactam of a compound of Formula (17) or (18) with sodium in liquid ammonia affords an optically pure lactam of Formula (19) or (20), respectively.

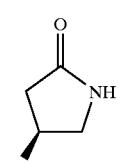
(19)

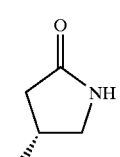
(20)

Treatment of a lactam of Formula (19) or (20) with a compound of Formula (21)

R2—X  (21)

in the presence of a base, such as sodium hydride or triethylamine, in a suitable solvent, such as dimethylformamide or methylene chloride, affords a compound of Formula (22) or (23).

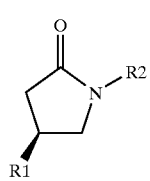
(22)

-continued

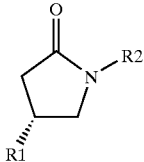
(23)

Conversion of a chiral lactam of Formula (22) or (23) to the chiral target compound of Formula (I) can then be achieved using reagents and conditions described above for transformation of a racemic compound of Formula (8) to a racemic compound of Formula (I).

The present compounds are further exemplified by the following Examples which are intended to be illustrative of the present invention and not limiting in any way.

EXAMPLE 1

Preparation of 2-[4-Butyl-1-(5-hydroxypentyl)-2-oxopyrrolidin-3-yl]-N-hydroxyacetamide 1(a) 1-(5-Benzyloxypentyl)-3-bromo-4-butylpyrrolidin-2-one A mixture of 4-butyldihydrofuran-2-one (4.26 g, 30 mmol) and phosphorous tribromide (0.052 mL, 0.55 mmol) was heated to 110° C. under argon. Bromine (1.29 mL, 25.2 mmol) was added slowly into the reaction mixture. The reaction was cooled slowly to 50° C. and dimethylformamide (0.003 mL) was added. After heating up to 90° C., thionyl chloride (2.58 mL, 30 mmol) was added slowly and the reaction was continued at the same temperature for 3h. Removal of the volatiles under reduced pressure gave 9.0 g (94%) of a brown oil, presumably 2,4-dibromo-3-butylbutyryl chloride, which was directly used for the next step without purification. A portion of this crude compound (2.5 g, 7.7 mmoL) was dissolved in chloroform (10 mL) and cooled to 0° C. To this cold solution was added 5-benzyloxypentyl amine (1.5 g, 7.7 mmol) in chloroform (10 mL). After 10 minutes, sodium hydroxide (0.34 g, 8.5 mmol) in water (3 ml) was added with vigorous stirring. The reaction was continued at 0° C. for 1 h, the organic phase was separated and washed with 0.5 N HCl (10 mL), water (10 mL), saturated NaHCO$_3$(10 mL), brine (10 mL) and dried (Na$_2$SO$_4$). After filtration, the solvent was removed under reduced pressure. The residue was dissolved in benzene (20 mL), cooled with an ice bath and treated carefully with small portions of sodium hydride (60% in mineral oil, 0.31 g, 7.7 mmol). After 30 minutes, the reaction mixture was poured into ice water, the organic phase was separated and washed with brine (10 mL), dried (Na$_2$SO$_4$). After filtration and removing the solvent, the residue was purified by flash column chromatography (silica gel, 1:3 EtOAc/hexanes) to afford 1.6 g (52%) of the title compound as a yellow oil: $^1$H NMR (CDCl$_3$) δ 7.34 (m, 5H), 4.53 (s, 2H), 4.32 (d, 1H), 3.65 (m, 2H), 3.48 (t, 2H), 3.29 (m, 2H), 2.48 (m, 1H), 1.24-1.70 (m, 12H), 0.91 (t, 3H). MS(ES) m/e 396 [M+H]$^+$.

1(b) 1-(5-Benzyloxypentyl)-4-butyl-2-oxopyrrolidin-3-yl]cetic acid, methyl ester A solution of t-butyl methyl malonate (0.69 g, 3.9 mmol) in dimethylformamide (10 mL) was treated with sodium hydride (60% in mineral oil, 0.16 g, 3.9 mmol) at 60° C. for 30 minutes. After cooling to room temperature, a solution of the compound of Example 1(a) (1.2 g, 3.0 mmol) in dimethylformamide (10 mL) was added dropwise. After stirring at room temperature overnight, the reaction mixture was diluted with ethyl acetate/hexanes (1:1, 100 mL) and washed with water (5×50 mL) and brine (50 mL), and dried (Na$_2$SO$_4$). After removing the solvent under the reduced pressure, the residue was dissolved in toluene (100 mL) and p-toluenesulfonic acid monohydrate (0.2 g, 1.0 mmol) was added. The resulting mixture was heated to reflux for 2h. After cooling to room temperature, the mixture was diluted with ethyl acetate (50 mL), washed with saturated NaHCO$_3$ (50 mL) and brine (50 mL), and dried (Na$_2$So$_4$). After removing the solvent under the reduced pressure, the residue was purified by flash column chromatography (silica gel, 1:4 EtOAc/hexanes) to afford 0.47 g (40%) of the title compound as a brown oil: $^1$H NMR (CDCl$_3$) δ 7.34 (m, 5H), 4.55 (s, 2H), 3.67 (s, 3H), 3.54 (m, 3H), 3.33 (m, 2H), 305 (m, 1H), 2.68 (m, 3H), 2.16 (m, 1H), 1.25-1.70 (m, 12H), 0.93 (t, 3H). MS(ES) m/e 390 [M+H]$^+$.

1(c) 2-[4-Butyl-1-(5-hydroxypentyl)-2-oxopyrrolidin-3-yl]-N-hydroxyacetamide

A solution of the compound of Example 1(b) (50 mg, 0.13 mmol) in methanol (3 mL) was stirred under a hydrogen balloon in the presence of palladium on activated carbon at room temperature overnight. The reaction mixture was filtered and concentrated to afford 37 mg (95%) of a clear oil, presumably (+/−)-[4-butyl-1-(5-hydroxypentyl)-2-oxopyrrolidin-3-yl]acetic acid, methyl ester, MS(ES) m/e 300 [M+H]$^+$. This compound was dissolved in dioxane (1.5 mL) and was treated with hydroxylamine in water (50%, 2 mL) at room temperature overnight. The reaction mixture was concentrated under vacuum and purified by automated HPLC to afford 25 mg (68%) of the title compound as a clear glass: $^1$H NMR (CD$_3$OD) δ 3.56 (m, 3H), 3.33 (m, 2H), 3.07 (m, 1H), 2.53 (m, 2H), 2.18 (m, 1H), 2.12 (m, 2H), 1.31-1.70 (m, 12H), 0.93 (t, 3H). MS(ES) m/e 301 [M+H]$^+$.

EXAMPLE 2

Preparation of 2-[(3R,4R)-4-Butyl-1-(5-hydroxypentyl)-2-oxopyrrolidin-3-yl]-N -hydroxyacetamide 2(a) (R)-3-Hydroxymethylheptanoic acid, (S)-1-phenylethylamide A mixture of (+/−)-4-butyldihydrofuran-2-one (3.9 g, 27.4 mmol), 2-hydroxypyridine (3.1 g, 32.9 mmol) and (S)-1-phenylethyl amine (7.8 mL, 60.3 mmol) in dry toluene (50 mL) was heated to reflux overnight. The reaction mixture was cooled to room temperature and diluted with ethyl acetate (100 mL), washed with 1 N HCl (2×50 mL) and brine (50 mL), dried (Na$_2$SO$_4$), and concentrated. The residue was purified by flash column chromatography (silica gel, 8:2 EtOAc/hexanes) to afford two compounds as white solids. The first eluted fraction was (S)-3-hydroxymethylheptanoic acid, (S)-1-phenyl-ethylamide (2.8 g, 39%) which is used in Example 3. $^1$H NMR (CDCl$_3$) δ 7.33 (m, 5H), 6.07 (bs, 1H), 5.11 (q, 1H), 3.63 (m, 1H), 3.48 (m, 1H), 3.29 (bs, 1H), 2.29 (m, 2H), 1.95 (m, 1H), 1.50 (d, 2H), 1.28 (m, 6H), 0.88 (t, 3H). MS(ES) m/e 264 [M+H]$^+$. The second eluted fraction was the title compound (2.6 g, 36%). $^1$H NMR (CDCl$_3$) δ 7.29 (m, 5H), 6.34 (bs, 1H), 5.09 (q, 1H), 3.64 (m, 1H), 3.57 (bs, 1H), 3.48 (m, 1H), 2.28 (m, 2H), 1.93 (m, 1H), 1.48 (d, 2H), 1.28 (m, 6H), 0.88 (t, 3H). MS(ES) m/e 264 [M+H]$^+$.

2(b) (R)4-Butyl-1-[(S)-1-phenylethyl]pyrrolidin-2-one

To a solution of di-t-butylazodicarboxylate (2.1 g, 9.1 mmol) in tetrahydrofuran (25 mL) under argon was added tributylphosphine (2.27 mL, 9.1 mmol). The mixture was stirred for 5 minutes and was added slowly to a solution of the compound of Example 2(a) (1.84 g, 7.0 mmol) in dry THF (10 mL) at 0° C. The reaction was warmed up to room temperature and the reaction mixture was stirred overnight. Saturated NaHCO$_3$ (100 mL) was added to the reaction mixture and the resulting mixture was extrated with CHCl$_2$ (2×100 mL). The combined organic extracts were dried (Na$_2$SO$_4$), filtered and concentrated. The residue was purified by flash column chromatography (silica gel, 1:4 EtOAc/hexanes) to afford 1.4 g (82%) of the title compound as a clear oil: $^1$H NMR (CDCl$_3$) δ 7.33 (m, 5H), 5.48 (q, 1H), 3.06 (t, 1H), 2.92 (t, 1H), 2.53 (q, 1H), 2.06 (m, 2H), 1.51 (d, 3H), 1.20-1.46 (m, 6H), 0.88 (t, 3H). MS(ES) m/e 246 [M+H]$^+$.

2(c) (R)-4-Butylpyrrolidin-2-one

To a solution of compound of Example 2(b) (1.4 g, 5.7 mmol) in dry tetrahydrofuran (10 mL) at −78° C. was condensed liquid ammonia (100 mL). Freshly cut sodium (0.66 g, 28.5 mmol) was added and the resulting mixture was stirred at −78° C. for 2h. The reaction was quenched with solid ammonium chloride. Ammonia was evaporated by warming up the reaction mixture slowly to room temperature. Water (50 mL) was added and the mixture was extracted with ethyl acetate (3×50 mL). The combined organic extracts were dried ($Na_2SO_4$), filtered and concentrated. The residue was purified by flash column chromatography (silica gel, 8:2 EtOAc/acetone) to afford 0.7 g (87%) of the title compound as a clear oil: $[\alpha]_D$=+0.950 (c=0.60, $CH_2Cl_2$) {lit. $[\alpha]_D$=−0.67° (c=0.60, $CH_2Cl_2$) for (S)-enantiomer, Meyers, A. I. and Snyder, L. 1993, J. Org. Chem. 58, 36-42}; $^1$H NMR ($CDCl_3$) δ 6.07 (bs, 1H), 3.48 (t, 1H), 3.02 (t, 1H), 2.45 (m, 2H), 1,99 (m, 1H), 1.22-1.50 (m, 6H), 0.90 (t, 3H). MS(ES) m/e 142 $[M+H]^+$.

2(d) (R)-1-(5-Benzyloxypentyl)-4-butylpyrrolidin-2-one

To a solution of the compound of Example 2(c) (0.42 g, 2.9 mmol) in dry dimethylformamide (10 mL) under argon was slowly added sodium hydride (60% in mineral oil, 0.14 g, 3.5 mmol) at 0° C. After stirring at 0° C. for 30 minutes, 5-benzyloxypentyl bromide (0.9 g, 3.5 mmol) was dropwise added. The resulting mixture was stirred at room temperature overnight and then diluted with ethyl acetate (50 mL). The organic solution was washed with water (4×30 mL), brine (30 mL), dried ($Na_2SO_4$) and concentrated. The residue was purified by flash column chromatography (silica gel, 1:1 EtOAc/hexanes) to afford 0.73 g (95%) of the title compound as a clear oil: $^1$H NMR ($CDCl_3$) δ 7.33 (m, 5H), 4.51 (s, 2H), 3.45 (m, 3H), 3.27 (t, 2H), 2.99 (dd, 1H), 2.52 (dd, 1H), 2.32 (m, 1H), 2.06 (m, 1H), 1.24-1.71 (m, 12H), 0.93 (t, 3H). MS(ES) m/e 318 $[M+H]^+$.

2(e) [(3R,4R)-1-(5-Benzyloxypentyl)-4-butyl-2-oxopyrrolidin-3-yl]acetic ccid, ethyl ester To a 2 M solution of lithium diisopropylamide (0.47 mL, 0.94 mmol) in THF (2 mL) at −78° C. under argon was slowly added a solution of the compound of Example 2(d) (0.25 g, 0.79 mmol) in dry THBF (3 mL). After stirring at the same temperature for 1 h. Bromo ethyl acetate (0.1 mL, 0.94 mmol) was dropwise added. The resulting mixture was continued to stir for 3h and then quenched with saturated ammonium chloride (10 mL). The mixture was extracted with ethyl acetate (3×10 mL), the combined organic extracts were dried ($Na_2SO_4$), filtered, and concentrated. The residue was purified by HPLC to afford 0.11 g (35%) of the title compound as a brown oil: $^1$H NMR ($CDCl_3$) δ 7.35 (m, 5H), 4.51 (s, 2H), 4.16 (q, 2H), 3.48 (t, 2H), 3.44 (m, 1H), 3.29(m, 2H), 2.98 (m, 1H), 2.75 (m,1H), 2.52 (m, 1H), 2.08 (m, 1H), 1.31-1.72 (m, 12H), 1.29 (t, 3H), 0.91 (t, 3H). MS(ES) m/e 404 $[M+H]^+$.

2(f) 2-[(3R,4R)-4-Butyl-1-(5-hydroxypentyl)-2-oxopyrrolidin-3-yl]-N-hydroxyacetamide Following the procedure of Example 1(c), except substituting the compound of Example 1(b) with the compound of Example 2(e), the title compound was prepared (50%).

$^1$H NMR ($CD_3OD$) δ 3.56 (m, 3H), 3.32 (m, 2H), 3.07 (m, 1H), 2.54 (m, 2H), 2.18 (m, 1H), 2.11 (m, 2H), 1.33-1.79 (m, 12H), 0.94 (t, 3H). MS(ES) m/e 301 $[M+H]^+$.

EXAMPLE 3

Preparation of 2-[(3S,4S)-4-Butyl-1-(5-hydroxypentyl)-2-oxopyrrolidin-3-yl]-N-hydroxyacetamide Following the procedure of Example 2(b)-2(f), except substituting (R)-3-hydroxymethylheptanoic acid (S)-1-phenylethylamide with (S)-3-hydroxymethylheptanoic acid, (S)-1-phenylethylamide, the title compound was prepared. It has the same $^1$H NMR and MS as the compound of Example 2(f).

With appropriate manipulation and protection of any chemical functionality, synthesis of the remaining compounds of Formula (1) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

The present compounds are useful for the treatment of bacterial infections including but not limited to respiratory tract infections and/or Gram positive infections.

Compounds of Formula (I) and their pharmaceutically acceptable salts may be administered in a standard manner for antibiotics, for example orally, parenterally, sublingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free acid. The daily dosage regimen for parenteral administration is suitably about 0.001 mg/Kg to 40 mg/Kg, of a compound of Formula (I) or a pharmaceutically acceptable salt thereof calculated as the free acid. the daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay

S. aureus or E. coli PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp.180–182, with minor modifications. The reaction mixture is contained in 50 uL with 50 mM potassium phosphate buffer (pH7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: Staphylococcus aureus Oxford, Staphylococcus aureus WCUH29, Enterococcus faecalis I, Enterococcus faecalis 7, Haemophilus influenzae Q1, Haemophilus influenzae NEMC1, Moraxella catarrhalis 1502, Streptococcus pneumoniae 1629, Streptococcus pneumoniae N1387, Streptococcus pneumoniae N1387, E. coli 7623 (AcrABEFD+) and E. coli 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to formula (1):

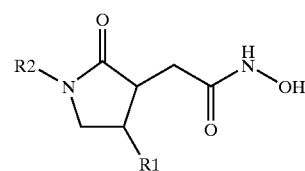

wherein:
R1 is selected from the group consisting of $C_{1-6}$alkyl, —$C_{1-2}$alkylAr, and Ar;
R2 is selected from the group consisting of hydrogen, $C_{1-6}$alkyl, —$(CH_2)_m$OH, —$(CH_2)_n$Ar', —$(CH_2)_n$Het, —Ar', —$SO_2$R3, —C(O)R3, —C(O)NHR3, —C(O)OR3, —CH(R4)CONR5R6, and —CH(R4)$CO_2$R7;
R3 is selected from the group consisting of $C_{1-6}$alkyl, —$C_{1-2}$alkylAr', and Ar';
R4 is hydrogen, or $C_{1-6}$alkyl;
R5 and R6 are independently selected from the group consisting of hydrogen, $C_{1-6}$alkyl, —$C_{1-2}$alkylAr', and Ar'; or R5, R6 together form a five or six membered cycloalkyl ring which is optionally mono-substituted by —$CH_2$OR7;
R7 is selected from the group consisting of hydrogen, and $C_{1-3}$alkyl;
Ar is selected from the group consisting of phenyl, furyl, and thienyl, all of which may be optionally substituted by one or more $Z_1$ groups;
Ar' is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl, all of which may be optionally substituted by one or more $Z_2$ groups;
Het is selected from the group consisting of tetrahydrofuranyl and piperidinyl;
$Z_1$ is independently selected from the group consisting of $C_{1-3}$alkyl, —CN, F, Cl, Br, and I;
$Z_2$ is independently selected from the group consisting of $C_{1-6}$alkyl, —OR2,
—$(CH_2)_n$$CO_2$R4, —C(O)NR5R6, —CN, —$(CH_2)_n$OH, —$NO_2$, F, Cl, Br, I, —NR5R6, and —NHC(O)R1;
m is 2 to 5;
and
n is 0 to 5.

2. A compound according to claim 1 selected from the group consisting of:
2-[4-Butyl-1-(5-hydroxypentyl)-2-oxopyrrolidin-3-yl]-N-hydroxyacetamide;
2-[(3R,4R)-4-Butyl-1-(5-hydroxypentyl)-2-oxopyrrolidin-3-yl]-N-hydroxyacetamide; and
2-[(3S,4S)-4-Butyl-1-(5-hydroxypentyl)-2-oxopyrrolidin-3-yl]-N-hydroxyacetamide.

3. A method of treating a bacterial infection by administering to a subject in need of treatment a compound according to claim 1.

* * * * *